United States Patent [19]

Blitzer

[11] Patent Number: 4,947,832
[45] Date of Patent: Aug. 14, 1990

[54] APPARATUS AND METHOD FOR TREATING OR RELIEVING COLICKY INFANTS

[76] Inventor: Avrum H. Blitzer, 37 Brookside Blvd., West Hartford, Conn. 06107

[21] Appl. No.: 123,928

[22] Filed: Nov. 23, 1987

Related U.S. Application Data

[63] Continuation-in-part of Ser. No. 935,405, Nov. 26, 1986, abandoned.

[51] Int. Cl.$^5$ ............................................. A61H 1/00
[52] U.S. Cl. ......................................... 128/33; 128/36
[58] Field of Search ............... 128/33, 1, 34, 36, 24 R, 128/44, 51, 52

[56] References Cited

U.S. PATENT DOCUMENTS

| | | | |
|---|---|---|---|
| 1,638,025 | 8/1927 | Everts | 128/33 |
| 2,112,367 | 3/1938 | Hyter | 128/33 |
| 2,765,786 | 10/1956 | Blong | 128/33 |
| 2,773,498 | 12/1956 | Himmelman | 128/33 |
| 2,790,440 | 4/1957 | Adair | 128/33 |
| 2,859,731 | 11/1958 | Sutton | 128/33 |
| 2,932,821 | 4/1960 | Horton | 128/32 |
| 3,298,363 | 1/1967 | Parkin | 128/33 |
| 3,311,935 | 4/1967 | Petty | 128/33 |
| 3,419,923 | 1/1969 | Cowan | 128/33 |
| 3,872,526 | 3/1975 | Betts | 128/33 |
| 3,955,222 | 5/1976 | Pater | 128/33 |
| 3,970,077 | 7/1976 | Dahl | 128/33 |
| 4,048,684 | 9/1977 | Korner et al. | 128/33 |
| 4,620,334 | 11/1986 | Robinson | 128/33 |
| 4,681,096 | 7/1987 | Cuervo | 128/33 |

OTHER PUBLICATIONS

Pediatrics, 1982, vol. 70, No. 6, pp. 864–869, "Effects of Water Beds on the Sleep and Motility of Theophylline-Treated Preterm Infants", Korner et al.

Primary Examiner—Edgar S. Burr
Assistant Examiner—Huong Q. Pham
Attorney, Agent, or Firm—Parmelee, Bollinger & Bramblett

[57] ABSTRACT

A colicky infant's vestibular and auditory centers are stimulated mechanically to simulate womb conditions to ease the transition from womb to postgestational life. In this soothing method an infant is placed in a crib with a mattress and having padded protective sides assuring appropriate positioning on the mattress, to which is imparted a regular, repetitive low frequency sine wave motion progressively traveling longitudinally thereof with simultaneous vibrations, whereby the infant experiences gentle, low frequency, regular, progressive, traveling sine wave motion plus hearing and sensing subdued vibrations like sensations previously experienced in the womb. The protective padded sides encircling the infant offer a warm enclosure while subduing or muffling exterior sounds. The illustrative apparatus includes an upper, mattress-supporting layer having a longitudinal series of transverse slats, gently moved up and down by motor-driven cams providing a distributed drive producing regular, repetitive, progressively traveling sine wave motion simulating peristalsis effects of an instenstine near a uterine wall. This support layer is also driven by vibrators simulating inter-uterine pulsations of a mother's blood, heartbeat, body movements, etc. A one-inch thick foam mattress covering the slats provides the longitudinally traveling sine wave motion undulating up and down about 2 to 7 millimeters (preferably 3.5 to 6.5 mm) at about 7 to 20 cycles per minutes, optimally about 8 to 12 cycles per minute, with wave length from about 24 inches to about 3 inches, and presently preferred from about 18 inches to about 4 inches.

20 Claims, 2 Drawing Sheets

APPARATUS AND METHOD FOR TREATING OR RELIEVING COLICKY INFANTS

RELATED APPLICATION

This is a continuation-in-part of application Ser. No. 935,405 filed Nov. 26, 1986.

FIELD OF THE INVENTION

This invention relates to a method and apparatus for treating or relieving colicky infants by stimulating the infant's vestibular and auditory centers to recapitulate the womb with a mechanically reproduced, progressively traveling sine wave motion, vibration and noise system. The underlying concept is the belief that infant colic symptoms result from an inability of the newborn to integrate all of the novel environmental and physical stimuli of the suddenly new extra-uterine habitat. The crying and apparent discomfort of the infant are believed to result from the infant's inability to understand and to adapt to the infant's own fledgling nervous system and its responses to this new extra-uterine world. The progressively traveling sine wave motion is a mechanical analogue of the amnionic fluid that suspended the infant so safely within the mother's womb and more importantly, provided the vestibular neurologic stimulation that the child was so accustomed to during maturation in-utero. It is to be noted that early neurologic centers that are operational in the fetus are the vestibular and auditory nerves. Thus, the underlying concept of the invention is to provide a mechanical analogue of the in-womb experience, thereby allowing the newborn to regress to an earlier and more secure and experienced developmental level (to return to the in-utero experience). Thus, the infant can be comfortably helped to complete, or at least more fully to develop the baby's neurological system so as to make the transition from the womb to the outside world less distressingly abrupt and with a more relaxed and comfortable body, i.e., to provide a more gradual transition to the new extra-uterine circumstances.

BACKGROUND

Colic is a physical condition in infants characterized by intense crying generally thought to be caused by spasmodic contractions of one of the hollow organs, such as the stomach, intestines, etc. Colic in infants, which often occurs and is limited in duration from near zero to about six months, is sometimes attributed to gas formed by excessive swallowing of air or inadequate digestion of milk. Whatever the cause, the colicky infant cries almost incessantly, producing sustained suffering for the infant as well as great anxiety and tension in the infant's family. Since there are no known long-term sequelae or consequences from infant colic, research in this area has been limited, and accordingly, other than dietary manipulation, no adequate therapeutic interventions have been established for effectively dealing with the problem of the colicky infant.

In U.S. Pat. No. 4,681,096 - Cuervo, a method and apparatus are provided for soothing and pacifying crying and colicky infants by imparting a rhythmic cyclic motion of displacement to to the surface on which the infant is supported. A motor in a housing is attached to the bed springs. This motor has a rotatable shaft carrying at least one eccentrically positioned weight which is positioned on a revolving arm by means of a set screw. This revolving eccentric weight imparts a rhythmic cyclic motion of displacement of the surface on which the infant is supported. The amplitude of displacement of the surface and its cyclic frequency is determined by the heaviness of the eccentric weight (or weights), the position of this weight (or weights) on the arm (or arms), and the speed of the motor. Any displacement is concentrated and greater in the vicinity of the location where the motor housing is attached to the springs. At the same time a sound generator produces audible sounds in a frequency range "between about two hundred and about four thousand Hertz" at an intensity of 60 to 80 decibels in order to emulatethe "wind motion sounds outside of a moving automobile traveling on the highway at 45-55 miles per hour." (Col. 6, 39-41). In U.S. Pat. No. 4,681,096 - Cuervo appears this teaching in Column 6, lines 12-26:

"In a test group of infants it has been found that relief of discomfort, fussiness, and colicky distress can be predictably relieved in a significantly large percent (90%) of test situations when rhythmic cyclic motion of displacement is imparted to the substrate at a frequency between about twenty-five cycles per second and about forty-three cycles per second with the amplitude of displacement between one eighth of an inch and about one hundredth of an inch."

"On the other hand, with other frequency or displacements outside of the range of practice of this invention, such predictably favorable therapeutic effects can not be obtained. As experience has shown in the prior art practices, many frustrating unsuccessful circumstances will result."

Moreover, in this U.S. Pat. No. 4,681,096 there is a timer 58 "provided in the power supply cord 50 or battery providing the capability of determining and adjusting the amount of time that power is supplied to the" motor, "so that" the motor "can be conveniently operated for a specified and predetermined period of time," (Col. 5, lines 28-32) usually in a range of about one-half hour.

SUMMARY OF THE DISCLOSURE

It is believed by the present inventor that colicky infants are unprepared to make the sudden transition from inside the womb to post-gestational life and the purpose of the invention is to aid the infant in making a gradual transition or conversion from inside the womb to the outside world. In other words, the colicky symptoms of the infant result from an inability of the newborn to integrate all of the novel environmental and sudden physical simuli of this abruptly new extra-uterine habitat. The present inventor believes that the infant's crying and apparent discomfort result from an inability to understand and adapt to the infant's own incompletely developed nervous system and its responses to the suddenly imposed new world outside of the amnionic fluid and the sounds and motions experienced while safely supported within this liquid during maturation in the womb. Unlike previous approaches such as the above-referenced Cuervo disclosure which attempts to simulate an automobile ride, the present invention is directed to simulating the environment of the amnionic fluid in which the infant was suspended in the mother's womb and which provided the infant with the vestibular neurologic stimulation that the infant was so accustomed to during maturation in-utero. Early neurological centers that are operational in the fetus are the vestibulary and auditory nerves. Hence, for a relatively long time the maturing fetus has been aware of its head motions and sounds in the amnionic fluid. Moreover, during the later stages of pregnancy the baby's head is down in the womb and whenever the mother walks, the pelvic cavity rocks back and forth stimulating the vestibulary nerves. Thus, it is believed that recreating the uterine environment and allowing the newborn infant to regress into that secure experience in effect enables the newborn infant's nervous system to bridge the drastic changes in environment occurring on birth, with which I believe the colicky infant is unable to cope.

Accordingly, it is an object of this invention to provide a new method and apparatus to relieve the apparent physical and psychological suffering of the colicky infant and the anxious family concerned for the newborn child.

A further object of this invention is to provide a new method and apparatus which simulates the infant's prior experiences in the womb and provides a means for gradually converting the environment of the infant from the gentle, soothing experiences within the womb of the mother to the outside world in a safe and sanitary manner.

Still another object of this invention is to provide a new method and apparatus for treating or relieving colicky infants which may be incorporated or attached to an infant crib, with the mechanical units being carefully isolated from the infant to obviate any risk of injury to the infant being treated.

In carrying out this invention in one illustrative embodiment thereof, a mattress apparatus is provided for treating or relieving colicky infants by simulating the intra-uterine environment of the unborn child which includes a bed or crib mattress support apparatus having an upper layer adapted to have a mattress positioned thereon. A series of movable strips are arranged transverse to the longitudinal dimension of this upper layer with distributed drive means for sequentially moving these movable strips up and down in sequence in a repetitive, gentle, progressive, traveling sine wave motion. Simultaneously, vibrating means may vibrate this upper layer, whereby the mattress positioned on this upper layer is simultaneously moved with a progressively traveling sine wave motion while being vibrated, and a soothing, throbbing, humming sound is also generated thereby simulating the womb environment. The upper surface of a one-inch thick foam mattress undulates up and down about 2 to 7 mm and preferably 3.5 to 6.5 mm in providing the progressively traveling sine wave motion, while the deflectable strips or slats themselves located beneath the mattress are being moved up and down about one-quarter to about three-eighths of an inch (about 6 to 10 mm). This traveling sine wave has a wave length in the range from about 24 inches to about 3 inches, and the presently preferred range is from about 18 inches to about 4 inches.

The bed is partially enclosed with protective padded sides of fire retardant material to ensure the centered postioning of the infant on the mattress resting on the upper layer and for concentrating the sound of vibration in a surrounding or enclosing configuration which muffles sharp environmental sounds originating outside of the crib, for more nearly simulating the muffled enclosed sounds which occurred in the womb where the colicky infant recently resided.

BRIEF DESCRIPTION OF THE DRAWINGS

The invention, together with further objects, aspects, advantages and features thereof may be better understood from the following description considered in conjunction with the accompanying drawings.

DESCRIPTION OF THE PREFERRED EMBODIMENTS

Figure 1:
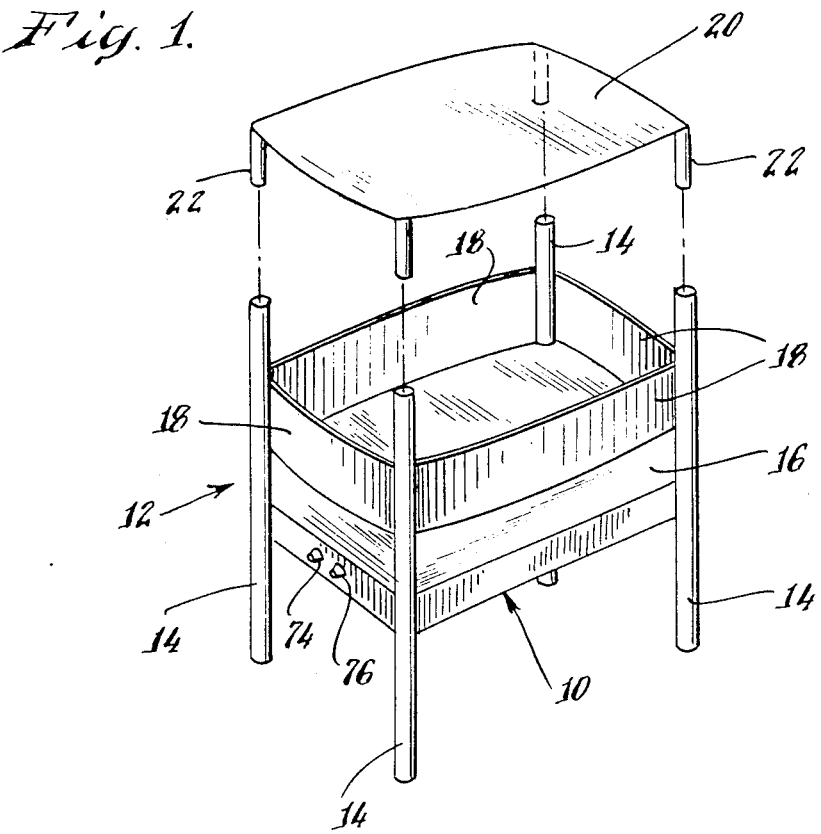
FIG. 1 is a perspective view showing an infant bed or crib with the apparatus embodying the present invention incorporated therein.

Referring first to FIG. 1, apparatus, which is specifically designed to stimulate the infant's vestibular and auditory centers and employing the method of the invention, recreates or simulates the motion conditions previously experienced by the baby in the womb and is referred to generally by the reference numeral 10. This apparatus 10 is incorporated into a bed or crib 12 having legs 14 and a mattress 16. The mattress 16 may be a part of the apparatus 10 in the form for example, of fire retardant foam padding, or the mattress 16 may be a separate mattress as long as it is capable of being manipulated in the manner to be described. In other words, the mattress 16 should not be so springy, thick and soft that it damps out or absorbs too much of the mechanical motions and sounds desired to be imparted to the infant.

The crib or bed 12 has protective upstanding padded sides 18 to insure that the infant placed in the crib remains safely and appropriately positioned in central location above the apparatus 10. The crib 12 may also have a canopy 20 with a plurality of mounting pegs 22 which may be inserted in sockets in the tops of the legs 14 of the crib to position the canopy thereon and partially enclose the crib in order to enhance the internal environment of the crib with respect to sound emanating from the apparatus 10, as will be explained hereinafter. The canopy 20 acts to provide a roof over the crib forming an acoustic reflector for internal sounds, while excluding noises coming from outside of the crib. The canopy 20 is intended not to totally enclose the crib, because access over the protective side walls 18 to the inside of the crib is required to care for and observe the infant positioned therein. The protective side walls 18 and the canopy 20 serve to exclude outside noises and to provide a semi-enclosed controlled acoustic environment.

The apparatus 10 including the mattress 16 may be incorporated in and/or removably installed in standard size cribs for home or hospital. Thus, the apparatus 10 may be positioned in the frame of a standard crib or may be designed and incorporated as a permanent installation for a crib, for example, intended to be repeatedly used in hospitals. The purpose of the apparatus 10 is to provide a traveling (progressively moving at a uniform rate) sine wave motion along with simultaneous vibration and accompanying sounds which combination of traveling sine wave motion, vibration and throbbing sounds generated by the apparatus 10 are designed to simulate the intra-uterine environment of the unborn child.

Figure 2:
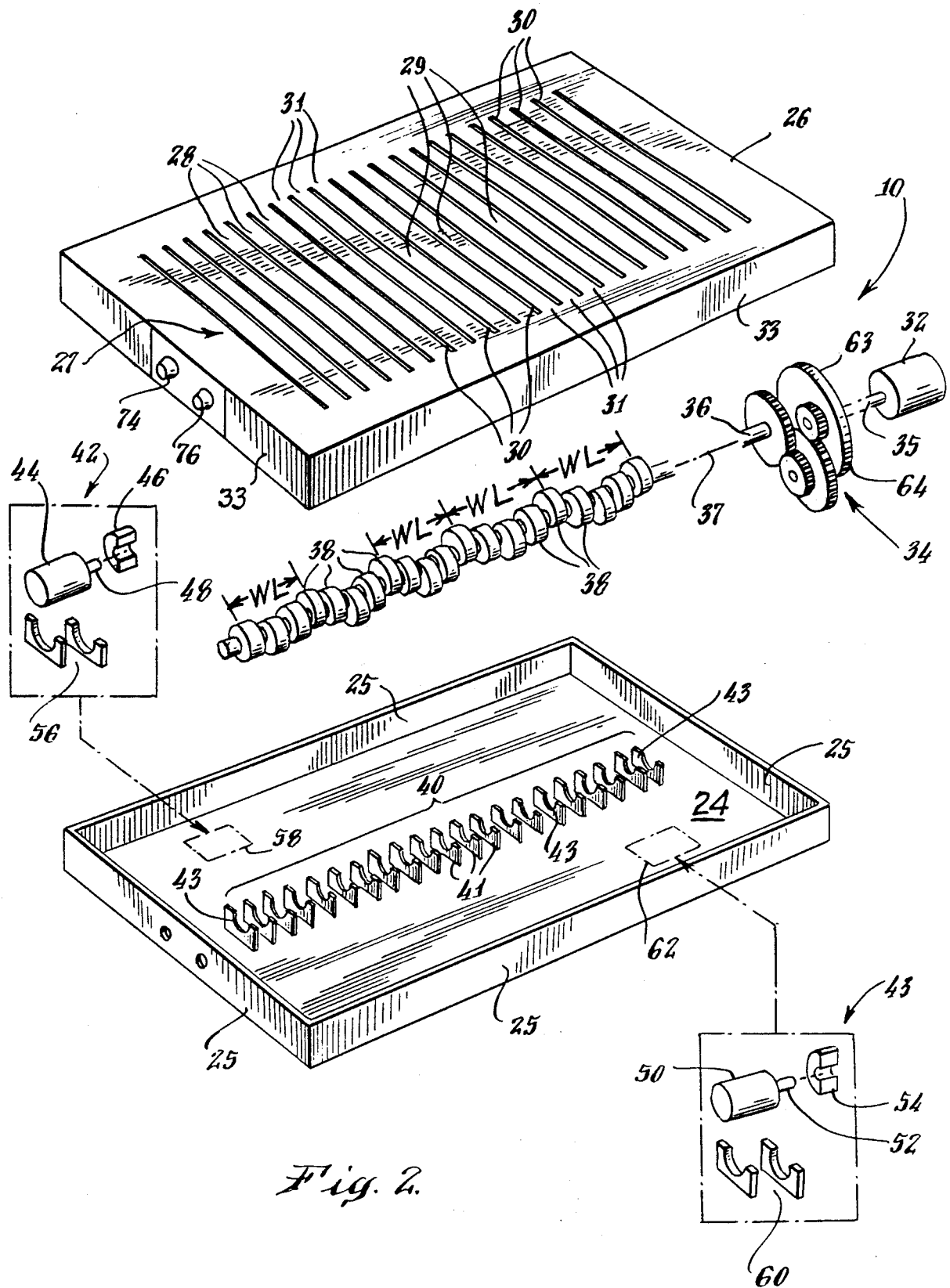
FIG. 2 is an exploded perspective view of the mechanical apparatus for producing a gentle fluid-type repetitive, traveling sine wave motion and simultaneous vibration of the mattress in the crib illustrated in FIG. 1, while also providing a repetitive, soothing sound.

Accordingly, the infant while lying on the apparatus 10 experiences a gentle, fluid-like or peristalsis-like traveling sine wave motion as well as having a throbbing sound and sensing a subdued vibration. The sine-wave-motion is a subtle, repeated, low frequency traveling wave form, preferably a uniformly longitudinally advancing moving sine wave, generated for traveling progressively along the longitudinal axis of the mattress 16 with a preferred frequency of about 7 to 20 cycles per minute, with the optimum being in the range from about 8 to 12 cycles per minute. The apparatus of FIG. 2 is an illustrative embodiment of the invention, which may be used to produce the consistent, predictable traveling fluid-like, sine wave motion and vibration and throbbing sound of the type desired, although it will be understood that other mechanical means to provide a distributed drive may be used so long as the resulting simultaneous, repetitive progressively traveling sine wave motion of the above-specified frequency and vibration and sound are produced in the method and manner contemplated by the present invention. A traveling sine wave advances along a path. In accord with the present invention, the path along which the traveling sine wave advances is the horizontal longitudinal axis of the crib mattress. It is to be noted that each point on the surface of the mattress is moving up and down, yet the wave motion as a whole is advancing at a uniform rate along the horizontal longitudinal axis of the mattress, somewhat like waves advancing at a uniform rate along the surface of a body of water.

As used herein the term "traveling sine wave" means a fundamental form of wave motion that results from periodic oscillations in which the amplitude of up and down displacement at each point along the horizontal path of travel is proportional to the sine of the continuously and uniformly increasing phase angle of the displacement, and the phase angle of each further ahead point along the path of travel is uniformly advanced relative to each preceding point.

Referring now to FIG. 2, the apparatus 10 includes a base frame platform 24 for housing and holding a plurality of motors and other mechanical structures for generating the desired traveling sine wave mechanical motion and vibrational modes and the sound desired. This base platform 24 includes upturned shallow boxlike sides 25. Positioned above the base frame 24 is a horizontal deck-like support surface or upper layer 26 having a plurality of elongated parallel horizontal strips or slats 28 extending transversely across this rectangular plate formed and separated by elongated parallel slots 30 cut into this plate 26 and extending over a substantial portion of the width of this plate, e.g. slots extending more than about 60% of the plate width. This row 27 of parallel slats or strips 28 extends for a significant portion of the length of the rectangular upper layer 26, for example, the row 27 extends more than about 25% of the plate length. The upper layer 26 is preferably made of a stiffly flexible thin plastic plate permitting a limited amount of up and down resilient flexing movement in the up and down direction of each horizontal strip 28. The central region 29 of each strip 28 will deflect resiliently up and down, while the ends 31 of each strip, which are integral with the remainder of the plate 26, will deflect insignificantly. By deflecting the row 27 of strips 28 up and down by a distributed drive in repeatable progressive sequence, an effective advancing traveling sine wave motion is generated in the longitudinal direction of the layer 26, i.e, in a direction perpendicular to the length of the strips 28.

Such a regular, repetitive traveling sine wave of predetermined wave length is achieved in one means as shown in FIG. 2 by a direct current (DC) motor 32 driving a shaft 36 through a speed-reducing torque-increasing gear reduction transmission 34 with a plurality of cams 38 mounted on the rotatable drive shaft 36. These cams 38 are circular and are eccentrically offset from their common axis of rotation 37, namely, the axis of the driven shaft 36. The shaft 36 and the eccentric offset cams 38 are positioned on the base frame 24 for rotatable movement while freely resting in a cradle 40. The motor 32 is a small, low-voltage, battery-energizable motor having a permanent magnet field structure. The cradle 40 extends longitudinally of the base frame 24 and comprises a plurality of upstanding brackets 41 arranged in a row parallel with and aligned beneath the central portion 29 of the row 27 of deflectable strips 28. Each of the brackets 41 has an upwardly facing U-shaped saddle surface 43 on which the cam shaft 36, 38 freely rides as the shaft 36 is turned around its axis 37 at a preferred speed in the range from about 7 to about 20 revolutions per minute, and optimally at about 8 to 12 RPM. This slow turning rate insures a regular, repetitive traveling sine wave which closely simulates a water medium analagous to the womb. The upper layer 26 has shallow downturned boxlike sides 33 which overlap the sides 25 of the base 24, when the upper layer 26 is mounted onto the base 24 in operating position, thereby providing a totally enclosed, shallow box-like enclosure for all of the moving parts.

The offset cams 38, when revolving in the cradle 40 and with the upper plate or layer 26 positioned on the base plate 24 are in contact with respective ones of the strips 28 for gently deflecting and moving them up and down using this distributed drive in sequence depending on the eccentric orientation of the respective associated cam on the shaft 36. There is one cam 38 for each strip 28, with a repetitive predetermined progressive offset sequence or pattern in the cams' orientation on the shaft 36. A gentle, fluid-like traveling sine wave movement is thus generated progressing in a direction perpendicular to the strips 28 on the upper layer 26. These deflecting strips are in contact with a foam pad or mattress 16, as shown in FIG. 1. This distributed drive structure faithfully and reliably, repetitively reproduces the desired sine wave. Short sections of the shaft 36 located between successive cams 38 can bear on the saddle surfaces 43.

The traveling sine wave has a predetermined wavelength "WL" as determined by the cams 38 and the orientation of their eccentric high and low regions with respect to the axis 37. In this embodiment the wave length WL of the traveling sine wave is in the range from about 24 inches to about 3 inches, and the presently preferred range is from about 18 inches to about 4 inches. In other words, this wave length WL of the traveling sine wave is generally in a range comparable to somewhat more than the overall length of the infant from toe tips to somewhat less than the size of the baby's head from jaw to head top.

In this embodiment the distributed drive 36, 37, 38 is provided by a series of cams. It is to be noted that in lieu of the series of cams 38, a distributed traveling sine wave drive can be made by bending a stiff length of pipe or a stiff length of tubing into a sinuous shape wherein the high and low positions of the bends of this elongated stiff element are oriented eccentrically from the drive axis 37 in the same way as the cams 38. Fewer bearing saddles 43 than shown in FIG. 2 are used for rotatably supporting such a bent stiff traveling sine wave drive element on its bearing surfaces.

In this illustrative embodiment the cams 38 are uniformly spaced along the rotational drive axis 37 a distance of one inch from one cam center to the next cam center. The following table shows how various predetermined wave lengths WL of the traveling sine wave are predetermined by angular orientation of eccentric cams axially spaced one inch on centers.

TABLE I

| ANGULAR OFFSET BETWEEN SUCCESSIVE CAMS 38 | RESULTANT WAVE LENGTH "WL" OF TRAVELING SINE WAVE |
|---|---|
| 15° | 24" |
| 18° | 20" |
| 20° | 18" |
| 24° | 15" |
| 30° | 12" |
| 36° | 10" |
| 45° | 8" |
| 60° | 6" |
| 72° | 5" |
| 90° | 4" |
| 120° | 3" |

For example, in FIG. 2 there is shown an angular offset of 90° between successive cams 38, and thus the predetermined wave length WL of the traveling sine wave is 4 inches, because these 90° offset cams are spaced one inch on centers along their rotational axis 37. In preliminary tests this 4-inch WL has proven to be very effective in relieving or at least quieting a few colicky infants within a few minutes who had immediately previously been wailing with knees tightly doubled up against their stomachs.

In order to provide vibration along with the traveling sine wave motion, there are a pair of vibrators 42 and 43 mounted near two diagonally opposite corners of the rectangular base 24, directly under the upper layer or plate 26. Vibrator 42 includes a DC motor 44, similar to the motor 32, having a semicircular eccentric weight 46 mounted on its shaft 48. This vibrator 42 is mounted in the position 58 on the base 24. Vibrator 43 is of similar construction having a DC motor with a motor shaft 52 having a semi-circular eccentric weight mounted thereon. Motor 44 is fastened in a rigid support 56 secured to the base 24 as indicated by the dashed outline 58, while the other vibrator 43 is fastened in the same type of rigid support 60 secured to the base 24 as indicated by the dashed outline 62. The operation of the vibrators 42 and 43 is the same. A motor driving a semicircular weight produces an imbalance on the motor shaft due to unbalance of the centrifugal effects of the semi-circular eccentric configuration of the mass of the weight, causing vibrations which are transmitted through the motor and through its support into the base 24. By virtue of the fact that the upper layer 26 is closely mechanically fastened to the base 24 all around its perimeter by the sides 33 overlapping and being secured to the sides 25, the vibrations of the base 24 are transmitted very effectively into the upper layer or plate 26.

It is preferred that the vibrator motors 44 and 50 are rotating at a speed of at least about 600 RPM in order to provide a pleasant vibration action. Preferably, the speed will be less than about 4,000 RPM for generating vibrations which appear to be most effective. The rapid rotation of the motor shaft 48 or 52 carrying its eccentric mass 46 or 54, respectively, causes the motor shaft bearings and the motor 44 or 50 to give off a pleasant throbbing or humming sound which is pacifying and relaxing for the infant.

In view of the fact that the cams 38, turning and supported by the respective saddles 43 while lifting and deflecting the respective strips 28, impose variable mechanical loads on the transmission 34, the shaft 35 of the motor 32 carries a flywheel 63 connected to the power input gear 64 of the transmission 34. Thus, the small motor 32 is enabled to run at nearly constant speed in spite of the variable loads imposed on it.

Figure 3:
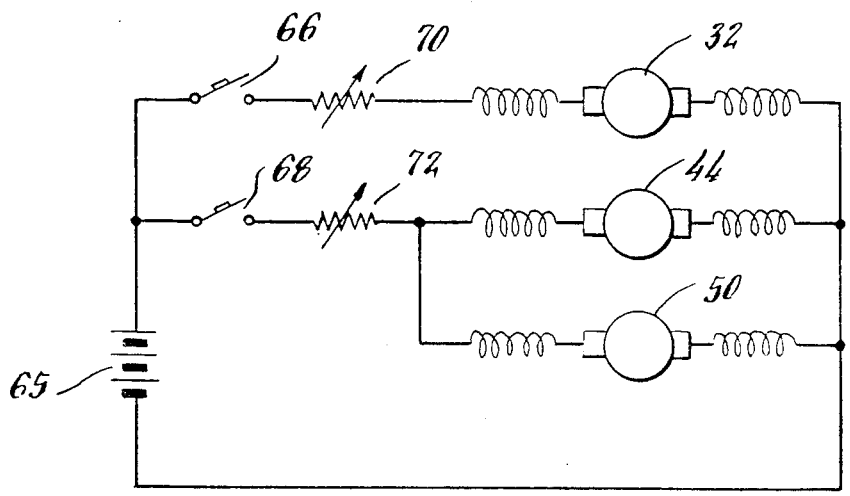
FIG. 3 is an electrical diagram illustrating one form of circuit means for providing the electrical drive for the apparatus illustrated in FIG. 2.

As will be seen in FIG. 3, the motion, vibration and sound generated by the apparatus 10 may be energized by a common power supply illustrated in FIG. 3 as a battery 65 which supplies electric power for the progressive motion motor drive 32 and for the vibrational motors 44 and 50. The power supply 65 does not require in excess of 12 volts which is obtained in the form of a battery pack. A battery pack is preferred because of its safety. It is possible to use a low voltage stepdown transformer connected to an ordinary 120 volt AC electric power outlet, in which case the motors 32, 44 and 50 are AC/DC type motors, but a battery power supply 65 is preferred. Separate ON/OFF switches 66 and 68 as well as separate variable resistor speed controls, 70 and 72 are provided for wave-motion drive motor 32 and for vibration drive motors 44 and 50, respectively. Switches 66 and 68 may be incorporated into the speed-control adjustable resistors 70 and 72, respectively to simplify the electrical controls. Thus, a pair of control knobs 74 and 76 (FIG. 2) are accessible at one end of the apparatus 10. These control knobs actuate the respective ON/OFF switches and the associated adjustable resistors for setting the desired motor speeds. Although not shown in FIG. 2, the battery pack 65, or step-down transformer, if utilized, is also housed in the base frame 24.

In operation, a colicky infant is treated or relieved and soothed by placing the colicky infant centered on the mattress 16 of the apparatus 10 with its encircling side walls 18. The knob controls 74 and 76 are turned to the desired settings thereby imparting a low frequency, gentle fluid-like progressive sine-wave motion traveling longitudinally to the mattress, while at the same time simultaneously subjecting the infant to vibrating motion with its accompanying throbbing, humming sounds. The fluid-motion which is a subtle sine-wave-form generated along the longitudinal axis of the mattress 16 has a frequency preferably of approximately 7 to 20 cycles per minute and optimally at about 8 to 12 cycles per minute and a wave length in the range from about 24 inches to about 3 inches and in the presently preferred range from about 18 inches to about 4 inches. The levels of sound are controlled so as to be soothing and comforting but not disturbing to the infant by controlling the speed of the vibrators with the speed control resistor 72.

The synergistic effects of the traveling sine wave motion, vibration and throbbing, humming sound are designed to simulate the conditions in the womb to which the unborn infant was subjected during gestation and therefore provide a transition from the womb to post-gestational life, thereby providing a gradual transition period from the mother to the outside world, instead of the abrupt change in environment brought on by the birth of the infant. The mechanical units may be modified or other types of mechanical structure may be utilized to simulate the desired sine wave cam motion, the vibration and the throbbing humming sound. All of the mechanical units are desirably isolated from the infant by the foam padding or by mattress 16 and the plate 24 which obviates any chance for injury to the infant by the moving parts. In addition, the infant is enclosed in the apparatus with protective side walls 18. Since the mattress sides 18 and all other materials are preferably made of fire retardant materials and the electrical power required is no more than 12 volts, there is no significant risk of fire or electrical hazard.

In a presently preferred embodiment the strips or slats 28 are deflected upwardly about ¼ to ⅜ of an inch (about 6 to 10 mm) when fully lifted by a cam 38. The springy resilience of the stiffly flexible plastic layer 26 returns the deflected strip back to its original straight condition as the rotating cam gently removes its lifting action from beneath the strip. A foam mattress one-inch thick on this layer 26 will provide an undulating traveling sine wave motion using a distributed drive in which the up and down movement of the upper surface of the mattress is in the range from about 2 to 7 mm and preferably in the range of 3.5 to 6.5 mm. The distributed drive of the rotating cams will cover a significant portion of the mattress length. This traveling sine wave has a length in the range from about 24 inches to about 3 inches, and the presently preferred range is from about 18 inches to about 4 inches.

Experimental trial has shown that this traveling sine wave is much more effective in pacifying or relieving a colicky infant than the vibrational motors 44 and 50. In fact, those vibrational motors may be shut off or omitted entirely, and the traveling sine wave alone is fully effective to produce the desired quieted and pacified and apparently relieved response in a colicky infant. The desired sound signature for the illustrative method and apparatus embodying the invention is a frequency of 80–12,500 Hertz and an intensity of about 40–60 decibels in the "A weighted mode". The "A weighted mode" is a reference standard of sound frequencies representing a bell-shaped curve representing the average human auditory spectrum.

In summary the apparatus incorporating the present invention provides the comfort of a portable crib mattress, may be used with standard size cribs and accordingly may be transported from one infant to another when the need for its use has terminated, since colic in infants is normally limited to less than a six-month period.

The mechanical mechanisms of the present invention are carefully isolated from the infant but yet sufficiently closely reproduce the general fluid and auditory stimuli of the amnionic sac that the soothing and comforting effects upon the infant with colic are truly amazing and must be seen to be appreciated. In addition, it is believed that the effects of any long term neurologic sequelae are very remote and much less than allowing the infant to cry or scream in discomfort, since the apparatus reproduces a stimuli analogous to the infant's intra-uterine habitat. The relief of the colicky condition of an infant by utilizing the present method and apparatus is advantageous. There is control of the immediate and sustained suffering of the infant as well as removing the resultant anxiety and tension of the family. The relief of the colicky condition may not only relieve the immediate physical and psychological suffering, but may also in effect offer some assistance to observers in understanding the further developmental and cognitive physiology of the previously suffering baby.

Since other changes and modifications varied to fit particular operating requirements and environments will be apparent to those skilled in the art, the invention is not considered limited to the examples chosen for purposes of illustration, and includes all changes and modifications which do not constitute a departure from the true spirit and scope of this invention as claimed in the following claims and equivalents thereto.

What is claimed is:

1. Apparatus for treating or relieving colicky infants by simultating an intra-uterine environment experienced prior to birth by an unborn child in a womb comprising:
    a frame for use in a bed adapted for having a mattress positioned thereon on which an infant with colic can be rested,
    said frame having a longitudinal direction,
    a series of upwardly and downwardly movble elements,
    said elements being arranged along the longitudinal direction of said frame, and
    distributed drive means acting on said movable elements for producing repetitive and sequential upward and downward motion by said movble elements of about 6 mm to about 10 mm for producing regular, repetitive, predetermined, uniformly advancing traveling sine-wave-like motion progressive in the longitudinal direction of said frame and having frequency in the range of about 7 to about 20 cycles per minute.

2. The apparatus as claimed in claim 1, in which:
    a mattress is positioned on said series of upwardly and downwardly movable elements, and
    the upper surface of said mattress is moved up and down by an amount in the range from about 2 millimeters to about 7 millimeters by said movble elements, and
    said traveling sine-wave-like motion has a predetermined wave length in the range from about 24 inches to about 3 inches.

3. The apparatus as claimed is claim 2, in which the upper surface of said mattress is moved up and down in the range from about 3.5 to about 6.5 mm.

4. The method for treating or relieving a colicky infant in an age range from age zero to six months comprising the steps of:
    placing the colicky infant on a support having a longitudinal direction with the infant's body extending generally horizontally longitudinally along the support,
    imparting a low frequency, repetitive regular and predetermined traveling sine-wave-like motion to said support traveling longitudinally along said support in a frequency range between 7 and about 20 cycles per minute with the amplitude of said traveling sine-wave-like motion being less than about 10 mm,
    whereby the colicky infant so positioned on said support will experience a gentle, longitudinally traveling continuous sine-wave-like motion, similar to a sensation which the infant previously experienced in the womb prior to birth.

5. The method for treating or relieving a colicky infant as claimed in claim 5 wherein:
said frequency range is from about 8 to 12 cycles per minute.

6. The method for treating or relieving a colicky infant as claimed in claim 4, in which:
said repetitive, regular, predetermined traveling sine-wave-like motion has a predetermined wave length in the range from abut 24 inches to about 3 inches.

7. The method for treating or relieving a colicky infant less than seven months old comprising the steps of:
placing the colicky infant an a support having a surface in supporting relation to the infant and having a longitudinal direction and with the infant's body being positioned generally horizontally longitudinally of said support, and
producing in said surface a repetitive predetermined traveling sine-wave-like motion traveling in said longitudinal direction and having a frequency in the range from about 7 to about 20 cycles, and
said repetitive predetermined traveling sine-wave-like motion having a predetermined wave length in the range from about 24 inches to about 3 inches.

8. The method as claimed in claim 7, in which:
said repetitive predetermined traveling sine-wave-like motion has an up and down amplitude of motion in the range from about 3.5 mm to about 6.5 mm.

9. Method as claimed in claim 7, in which:
said low frequency traveling sine-wave-like motion has an amplitude of movement up and down of a point on said support surface in the range of about 2 mm to about 7 mm.

10. Apparatus for treating or relieving a colicky infant having an age in the range from zero to six months after birth of such infant, said apparatus comprising:
support means having a support surface against which a body and head of a colicky infant can be rested,
said support surface having a predetermined direction for resting the colicky infant's body and head against said support surface with the colicky infant's body and head extending generally horizontally along said predetermined direction,
distributed drive means in driving relationship with said support surface,
said driving relationship of said distributed drive means extending along said support surface in said predetermined direction for a distance at least equal to a typical distance from a middle of a colicky infant's stomach to the top of the head, and
said distributed drive means producing predetermined movement of said support surface in a regular repetitive traveling sine wave motion having a wave length in the range from about 24 inches in said directions to about 3 inches.

11. The method as claimed is claim 10, in which:
said traveling sine-wave-like motion has a frequency in the range from about 7 to about 20 cycles per minute.

12. The method as claimed is claim 10, in which:
said traveling sine-wave-like motion has a frequency in the range from about 7 to about 20 cycles per minute, and
said traveling sine-wave-like motion has a predetermined wave length in the range from about 18 inches to about 4 inches.

13. Apparatus for treating or relieving a colicky infant as claimed is claim 10, in which:
distributed drive means produce motion having an amplitude between about 2 mm and 10 mm, and
said predetermined movement of said support surface in a regular repetitive traveling sine wave motion having a frequency in the range from about 7 to about 20 cycles per minute.

14. Apparatus for treating or relieving a colicky infant as claimed in claim 10, including:
means for producing vibration of said support surface with accompanying sound having a sound signature in a frequency of 80 to 12,500 Hertz and an intensity of about 40 to 60 Decibels in the "A weighted mode" reference standard of sound frequencies representing a bell-shaped curve representing average human auditory spectrum.

15. Apparatus for treating or relieving a colicky infant as claimed in claim 14, in which:
said distributed drive means produce motion having an amplitude between about 2 mm and 10 mm, and
said predetermined movement of said support surface in a regular repetitive traveling sine wave motion having a frequency in the range from about 7 to about 20 cycles per minute.

16. Apparatus for treating or relieving colicky infants by simulating an intra-uterine environment experienced prior to birth by an unborn child in a womb comprising:
a frame for use in a bed adapted for having a mattress positioned thereon on which an infant with colic can be rested,
said frame having a longitudinal direction,
a series of upwardly and downwardly movable elements,
said elements being arranged along the longitudinal direction of said frame,
distributed drive means acting on said movable elements form producing repetitive and sequential upward and downward motion by said movable elements of about 6 mm to about 10 mm for producing regular, repetitive traveling sine-wave-like motion progressive in the longitudinal direction of said frame and having frequency in the range of about 7 to about 20 cycles per minute,
said frame including a stiffly flexible layer,
said elements being integral strips of said layer,
said strips of said layer extending transversely relative to the longitudinal direction of said frame,
said strips being separated from one another by spaced slots extending transversely relative to the longitudinal direction of said frame for permitting resilient, individual up and down movement of each respective strip,
said distributed drive means including a motor having a drive shaft,
speed-reduction torque-increasing transmission means coupled to said drive shaft,
a plurality of wave-motion cams,
said cams being rotated about a common axis by said transmission means, and
respective cams being positioned beneath mid-portions of respective ones of said strips for causing movement of the individual strips up and down in predetermined sequence for imparting a traveling sine-wave-like motion to said strips and thus to a mattress positioned thereon.

17. The apparatus as claimed in claim 16, wherein:

said wave motion cams are eccentrically offset with respect to their common axis of rotation in a predetermined pattern for imparting a distributed traveling sine-wave-like motion to said strips, whereby said strips and the mattress positioned thereon move with a regular, repetitive traveling sine-wave-like motion.

18. The apparatus as claimed in claim 16, in which:

said regular, repetitive traveling sine-wave-like motion has a predetermined wave length in the range from about 24 inches to about 3 inches.

19. The apparatus as claimed in claim 16, in which:

said regular, repetitive traveling sine-wave-like motion has a frequency in an optimum frequency range of about 8 to about 12 cycles per minute.

20. The apparatus as claimed in claim 19, in which:

said regular, repetitive, predetermined uniformly advancing sine-wave-like motion has a wave length in the range from about 18 inches to about 4 inches, and means for producing a sound signature having a frequency of 80–12,500 Hertz and an intensity of about 40–60 decibels in the "A weighted mode".

* * * * *